(12) United States Patent
Uckelmann et al.

(10) Patent No.: US 8,884,186 B2
(45) Date of Patent: Nov. 11, 2014

(54) METHOD AND DEVICE USE TO PRODUCE A SET OF CONTROL DATA FOR PRODUCING PRODUCTS BY FREE-FORM SINTERING AND/OR MELTING, IN ADDITION TO A DEVICE FOR THE PRODUCTION THEREOF

(75) Inventors: Ingo Uckelmann, Bremen (DE); Frank Hagemeister, Bremen (DE); Carsten Vagt, Oysten (DE)

(73) Assignee: BEGO Medical GmbH, Bremen (DE)

( * ) Notice: Subject to any disclaimer, the term of this patent is extended or adjusted under 35 U.S.C. 154(b) by 1968 days.

(21) Appl. No.: 10/590,677

(22) PCT Filed: Feb. 16, 2005

(86) PCT No.: PCT/EP2005/050668
§ 371 (c)(1),
(2), (4) Date: Oct. 24, 2006

(87) PCT Pub. No.: WO2005/080029
PCT Pub. Date: Sep. 1, 2005

(65) Prior Publication Data
US 2007/0175875 A1    Aug. 2, 2007

(30) Foreign Application Priority Data

Feb. 25, 2004    (DE) .................. 10 2004 009 126

(51) Int. Cl.
| B29C 35/08 | (2006.01) |
| B23K 26/00 | (2014.01) |
| B22F 3/105 | (2006.01) |
| A61C 13/00 | (2006.01) |
| B29C 67/00 | (2006.01) |

(52) U.S. Cl.
CPC .......... B22F 3/1055 (2013.01); *B22F 2999/00* (2013.01); *B22F 2003/1057* (2013.01); *A61C 13/0013* (2013.01); *A61C 13/0018* (2013.01); *B29C 67/0077* (2013.01)
USPC ..................................... 219/121.85; 264/497

(58) Field of Classification Search
USPC ................. 219/69.12, 121.6, 121.16, 121.65, 219/121.69, 121.85, 497; 419/2, 6, 47; 156/62.2, 272.8; 700/118, 119; 264/497
See application file for complete search history.

(56) References Cited

U.S. PATENT DOCUMENTS

| 5,017,753 | A | * | 5/1991 | Deckard ...................... 264/497 |
| 5,183,598 | A | * | 2/1993 | Helle et al. ................... 264/401 |

(Continued)

FOREIGN PATENT DOCUMENTS

| EP | 1021997 A2 | 7/2000 |
| JP | 03-211040 | 9/1991 .............. B29C 67/00 |

(Continued)

OTHER PUBLICATIONS

Chabus, H., Internationale Recherchenbehorde Search Report, International Application No. PCT/EP2005/050668, Jun. 1, 2005, 6 pages.
Chabus, H., European Patent Office, Office Action, International Application No. EP 05 708 022.8, Feb. 6, 2007, 2 pages, English Translation, 2 pages.

(Continued)

*Primary Examiner* — Brian Jennison
(74) *Attorney, Agent, or Firm* — Kilpatrick Townsend and Stockton LLP (57) ABSTRACT

A method and apparatus used to produce control data for building up a product layer by layer using freeform sintering and/or melting with a high energy beam. The correspondingly controlled apparatus for production of the products is further disclosed. The high energy beam is applied under the guidance of the control data set. Before beginning the freeform sintering and/or freeform melting, a compensation data set and/or a compensation function to compensate for manufacturing related effects caused by the sintering and/or melting is determined. The control data set is based upon a product target geometry data set and the compensation data set and/or the compensation function.

14 Claims, 4 Drawing Sheets

(56) References Cited

U.S. PATENT DOCUMENTS

| | | | |
|---|---|---|---|
| 5,488,478 A * | 1/1996 | Bullock et al. | 356/604 |
| 5,555,481 A | 9/1996 | Rock | |
| 5,749,041 A | 5/1998 | Lakshminarayan | |
| 6,600,129 B2 * | 7/2003 | Shen et al. | 219/121.61 |
| 6,627,835 B1 * | 9/2003 | Chung et al. | 219/69.12 |
| 6,677,554 B2 * | 1/2004 | Darrah et al. | 219/121.85 |
| 6,974,323 B2 * | 12/2005 | Weigl et al. | 433/223 |
| 7,084,370 B2 | 8/2006 | Hagemeister et al. | 219/121.85 |
| 2002/0100750 A1 * | 8/2002 | Shi | 219/121.85 |
| 2002/0107604 A1 * | 8/2002 | Riley et al. | 700/121 |
| 2002/0145213 A1 * | 10/2002 | Liu et al. | 264/40.1 |

FOREIGN PATENT DOCUMENTS

| | | | |
|---|---|---|---|
| JP | 2002-115004 | 4/2002 | B22F 3/105 |
| JP | 2004-003018 | 1/2004 | B22F 3/105 |

OTHER PUBLICATIONS

Chabus, H., Internationale Vorlaufiger Bericht Uber Die Patentierbarkeit, International Application No. PCT/EP2005/050668, Apr. 11, 2006, 6 pages, English Translation, 3 pages.

Chabus, H. Internationale Recherchenbehorde Search Report, International Application No. PCT/EP2005/050668, 6 pages, English Translation, 7 pages.

* cited by examiner

METHOD AND DEVICE USE TO PRODUCE A SET OF CONTROL DATA FOR PRODUCING PRODUCTS BY FREE-FORM SINTERING AND/OR MELTING, IN ADDITION TO A DEVICE FOR THE PRODUCTION THEREOF

The invention relates to a method and a device for generating control data sets for the production of metallic and/or non-metallic products, in particular dental products or medical products, by freeform sintering and/or freeform melting by means of a high-energy beam, in particular a laser beam or electron beam, whereby a product is built up layer by layer, out of a material to be spread out in layers, by means of said beam guided with the help of a control data set. The method comprises the steps of loading a set of product target geometry data, which represents the target geometry of the product to be produced, and of generating the control data set on the basis of the product target geometry data set. Accordingly, the device for generating the control data sets comprises means for loading a product target geometry data set, which represents the target geometry of the product to be produced, and means for generating the control data set on the basis of the product target data set.

The invention further relates to an apparatus for producing such products by freeform sintering and/or freeform melting by means of a high-energy beam, in particular a laser beam or electron beam, whereby the apparatus comprises a beam source for generating this bean, a platform to accommodate a material to be added in layers, and as beam control a control system that guides the beam using data control to construct a product from the material layer by layer.

Methods, devices, and apparatus of this type are known in the art. Amongst other fields of application, they are used in the production of dental products, e.g. dental crowns, dental bridges, implants, etc. But they can also be used for other products.

But the required specifications for the precision and dimensional accuracy of these products are demanding. In particular in the field of dental product manufacturing one aims for tolerances of less than one tenth of a millimeter. However, such high precision can not be adequately obtained using the known sintering and melting systems.

Thus, the technical problem to be solved by the invention is the improvement of the dimensional accuracy of products produced by freeform sintering and/or freeform melting by means of a high-energy beam, in particular a laser beam or electron beam.

The invention provides a solution to this problem with a method of the above-mentioned type that additionally includes the steps of determining a compensation data set and/or a compensation function to compensate for manufacturing-related effects caused by the sintering and/or melting, and of combining the compensation data set with and/or applying the compensation function to the product target geometry data set to generate the control data set.

The invention further provides a solution to this problem with a device of the above-mentioned type that comprises means for determining a compensation data set and/or a compensation function to compensate for manufacturing-related effects caused by the sintering and/or melting, and means for combining the compensation data set with and/or applying the compensation function to the product target geometry data set to generate the control data set.

The invention finally provides a solution to this problem by means of a apparatus of the above-mentioned type, in which the control system comprises an above-described device for generating control data for beam guidance.

The invention is based on the understanding that manufacturing-related effects, i.e. effects caused by sintering and/or melting by means of a high-energy beam, can have negative effects on the dimensional accuracy of the products to be produced.

In freeform sintering or freeform melting by means of a high-energy beam, a product is created by a high-energy beam, e.g. a laser beam or electron beam, that irradiates a material—generally present in powder form—section by section, which heats and melts the material so that it bonds to the adjacent material.

However, an effect of this layer-by-layer construction is that in products with (lateral) sections inclined relative to the horizontal/vertical, a new layer to be applied will extend into a region that has no section of the product to be produced below it. In other words, the new layer to be produced projects laterally relative to the previously produced layer.

The invention has realized that material, which is melted in these projecting regions, will extend into the region of the layer below. In this region, so-called melting spherules will develop, i.e. spherical or partially spherical protuberances of the product that adulterate the dimensions of the product. Thus, the product will be thicker in these regions than originally planned.

The invention has also realized that the layer-by-layer construction and the bonding of layers at different temperatures will give rise to stresses within the layers due to different thermal expansion of the different layers. These stresses lead to deformations once the product is released from the carrier, the so-called substrate plate.

The influences, which are shown here as examples and which result in changes of the actually manufactured product relative to the planned product, are compensated for in the invention by at first determining a compensation data set and/or a compensation function. Subsequently, this compensation data set is combined with the product target geometry data set or the compensation function is applied to this product target geometry data set to generate the control data set, which is then used to control the high-energy beam during the sintering and/or melting process.

The compensation function or compensation data set determined in this manner can be used to almost completely compensate for the negative manufacturing-related effects of the sintering or melting by means of a high-energy beam, which substantially increases the dimensional accuracy.

The compensation data set or compensation function preferably is determined as a function of the size and shape or of an angle of inclination of a plane placed tangentially on an exterior surface of the product to be manufactured relative to a reference plane, e.g. a horizontal reference plane. This in particular serves to reduce a thickness of the product to be produced that is determined perpendicular relative to said tangential plane by application of the compensation data set or of the compensation function in dependence on this angle of inclination. In this manner it becomes possible to compensate for the influence of the above-mentioned melting spherules or partial melting spherules on the thickness of the product or product section to be produced. This almost completely prevents any errors in the product dimensions, in particular in the region of inclined sections.

The compensation function preferably is continuous and differentiable. In particular, the compensation function contains a polynomial of $2^{nd}$, $3^{rd}$, $4^{th}$, and/or higher degree. It has been shown that a compensation function of this type can be used to satisfactorily compensate for the effects of the various temperature-related and geometry-related stresses that are created due to the layer-by-layer construction of the product.

In a special embodiment, different compensation functions are used for different regions of the product to be produced. In a further embodiment, the degree of the polynomial of such a compensation function is also dependent on the respective region of the product to be produced.

In a further preferred embodiment, a lower-degree polynomial is used for simple-geometry regions of the product to be produced, while a higher-degree polynomial is used for complex-geometry regions of the product to be produced. The degree of the respective polynomial determines the computational effort. Naturally, the computational effort increases as the degree of the polynomial increases. Thus, it is advantageous to use a polynomial with the minimum feasible degree to still achieve satisfactory compensation results. But since the effects of the temperature-related stresses depend on the geometry of the product to be produced, the effects of the stresses will also be different in different regions of the product to be produced. Consequently, it is generally sufficient to use a simple compensation function for more compact geometries and to use a more complex compensation function for more complex or filigree geometries. This reduces the computational effort and in a practical manner increases the efficiency of the employed sintering or melting apparatus.

In a further special embodiment, the compensation function is applied to the product geometry data set only for certain regions of the product to be produced. For example, for dental bridges to be produced, one applies the compensation function to the product geometry data set only for the connecting regions of the dental prosthesis. In products of this type that are to be produced it has been shown that these connecting regions are subject to special stresses, whereas the effects of the temperature-related stresses are significantly less severe in the comparatively compactly formed regions that represent a tooth. Such a selective application of the compensation function also allows reducing the computational effort, which allows a better utilization of the computer power of the employed apparatus.

It is especially practical if the compensation data set and/or the compensation function is determined on the basis of at least one parameter out of a group of parameters that includes the following: modulus of elasticity, solidus temperature, thermal expansion coefficient, tensile strength, and elastic yield point of the material; a processing chamber temperature representing the temperature in a processing chamber surrounding the material to be processed; a processing temperature that represents the temperature of the region of the material irradiated by the high-energy beam, the layer thickness, representing the thickness of an applied material layer; the output power the beam source, in particular of the laser or electron beam source, or the power of the beam, in particular the laser beam or electron beam, during the process of sintering or melting; the traverse rate of the beam, the irradiation strategy; the geometry and in particular the height of the product to be produced as well as the type of secondary treatment after the sintering or melting. It has been shown that consideration of these parameters or a subgroup of these parameters allows achieving a substantial compensation for the manufacturing-related influences.

In a further preferred embodiment, a forming or already formed contour of the product is optically scanned during and/or after the irradiation of a material layer. The measurement data obtained in this manner are compared to the data of the product target geometry data set. If a deviation is detected, the control data set is corrected in accordance with the detected deviation. Such optical scanning of the product during its creation and the simultaneously performed correction of the control data can further increase the precision and dimensional accuracy of the product to be produced in a favourable manner.

Further preferred embodiments are illustrated in the embodiment examples, which are explained in more detail using the attached drawings.

Figure 1:
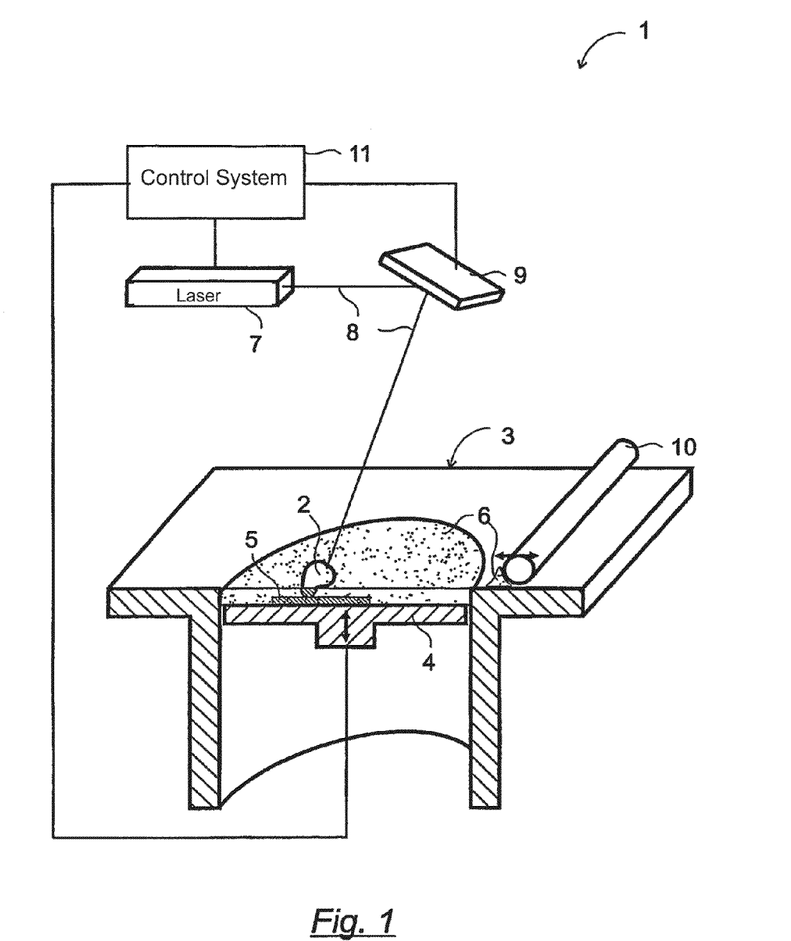
FIG. 1 shows a schematic side view of an apparatus for the production of products by freeform laser sintering and/or freeform melting according to an embodiment example of the invention.

FIG. 1 shows an apparatus 1 for producing metallic and/or non-metallic products 2, in particular dental products such as crowns, bridges, implants, etc., or medical products, such as for example prostheses, by freeform laser sintering and/or freeform laser melting. The apparatus 1 comprises a table 3 with a height-adjustable platform 4, on which a substrate plate 5 rests. The height of the platform 4 is adjustable stepwise via a not illustrated drive system, in particular in steps adapted to the size of powder grains of the material 6 present in powder form.

The apparatus 1 further comprises a laser 7 arranged above the table 3, for example a $CO_2$ laser, with a beam that is guided by a suitable device, in particular a computer-controlled mirror galvanometer 9.

The apparatus 1 further comprises a coating mechanism 10, which is used to distribute the material 6 in powder form uniformly over the surface of the table 3, so that in particular the space between the surface of the platform 4 and the surface of the table 3 is filled with material 6 in powder form up to the surface of the table 3.

Production of the product proceeds as follows: At first the platform 4 is in an upper starting position. Then the laser 7 is activated and its laser beam 8 is pointed at the material 6 in powder form. Due to the heat generated by the laser beam 7, the laser beam 7 compacts and melts the material in powder form 6, which—depending on the amount of energy applied to the material 6 in powder form—sinters or fuses with adjacent powder grains. The laser beam 8 is guided by means of a control data set. Following this guidance, the laser beam irradiates predetermined positions of the powder material 8. In the regions irradiated by the laser beam 8, a solid layer of fused or sintered material is created.

Once a layer has been completed, the laser 7 is deactivated and the platform 4 is lowered by a layer thickness, which for example can be adapted to the average diameter of the powder grains of the material 6. A new layer of powder material 6 is then applied and flattened by means of the coating mechanism 10. Then the laser 7 is activated again and the laser beam 7 is again computer-controlled to travel to predetermined positions, at which the material 6 in powder form is fused or sintered to the previously generated layer or to regions adjacent thereto or regions not adjacent thereto. This process of applying layers of starting material 6 in powder form and the sintering or melting of these layers to the previously applied layers by means of the laser beam 8 is carried out repeatedly until the product 2 has been formed in the desired shape.

The apparatus 1 comprises a control system 11, which in particular controls the activation and deactivation of the laser 7 as well as the positioning of the laser beam 8 via the mirror galvanometer 9, and the height adjustment of the platform 4. Coordinating these components of the apparatus 1 on the whole guarantees the desired formation of the products 2.

The control system 11 comprises means for reading in a data set of product target geometry data, which represent the target geometry of the product to be produced. Starting from these target geometry data, the control system computes a control data set that is used to guide the laser beam. The control data set for example contains data for adjusting the mirror galvanometer 10, which determines the impact point of the laser beam 9 on the uppermost layer of the material 6.

The control system 11 further determines a compensation data set and/or a compensation function for manufacturing-related effects that occur during laser sintering or laser melting and are described in the following. These compensation data are combined with the target geometry data set or the compensation function is applied to the target geometry data set in order to generate the previously explained control data set. In this manner, the manufacturing-related effects of the laser sintering or laser melting, which will be explained in more detail in the following, can be taken into account already prior to the production of the products 2 or prior to the creation of the product's 2 next layer to be formed.

Figure 2:
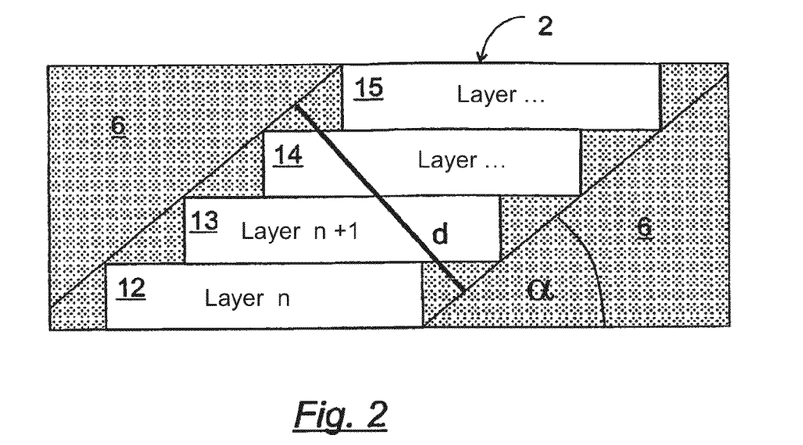
FIG. 2 shows a schematic side view to illustrate the layer-by-layer structure of products produced by means of an apparatus of FIG. 1, in accordance with an ideal theoretical model.

FIG. 2 serves as explanation of a first such manufacturing-related effect. FIG. 2 shows a section of an already laser-sintered or laser-melted product 2, which is created in several layers 12, 13, 14, 15. However, the layers 12 to 15 are not situated vertically on top of each other, but offset with respect to each other. The respective offset yields a slope with an angle α between a tangential plane placed against the ends of the layers and the horizontal plane, for example the top surface of the platform 4.

In the example shown in FIG. 2, the layers 12 to 15 all exhibit the same width, so that in an ideal case an inclined plate of width d is created, which will be oriented at an angle α relative to the horizontal plane.

Figure 3:
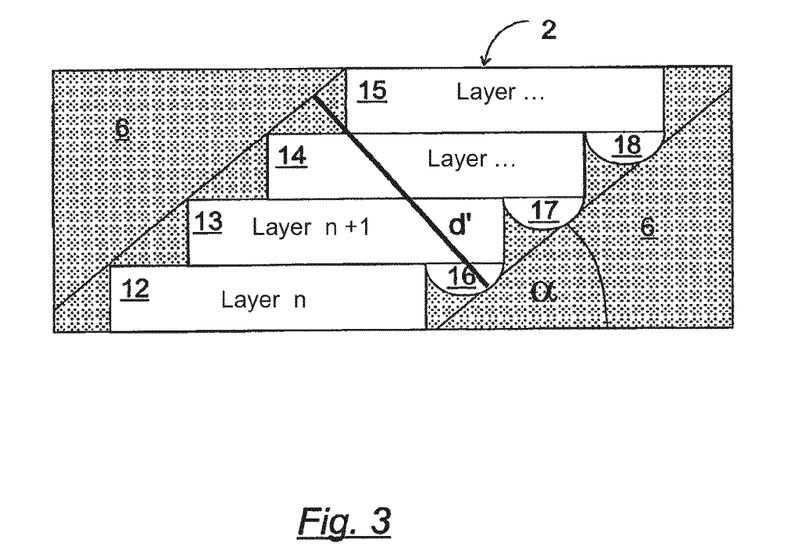
FIG. 3 shows a schematic illustration analogous to FIG. 2, of an actual produced product.

FIG. 3 shows a practical realization of the theoretical product shown in FIG. 2. At the right end of the layers 13 to 15, each of which is offset by a certain distance relative to the respective layer 12 to 14 below, so-called melting spherules or melting spherule sections 16, 17, 18 are formed during the laser sintering or laser melting. Material 6 melted in these regions does not only heat the material powder 6 within the thickness of a layer 13, 14, 15, but rather also the surrounding material powder 6, which as a result melts, flows downward in the liquid phase, and thereby forms the melting spherules 16, 17, 18.

The melting spherules 16 to 18 result in a thickness d' that is greater than the thickness d illustrated in FIG. 2.

This manufacturing-related influence on the thickness of the product to be produced depends—among other things—on the angle of inclination α. The greater the angle α, i.e. the angle between the tangential plane and the horizontal plane, the smaller will be the adulteration of the thickness d' relative to the theoretical thickness d illustrated in FIG. 2.

Figure 4:
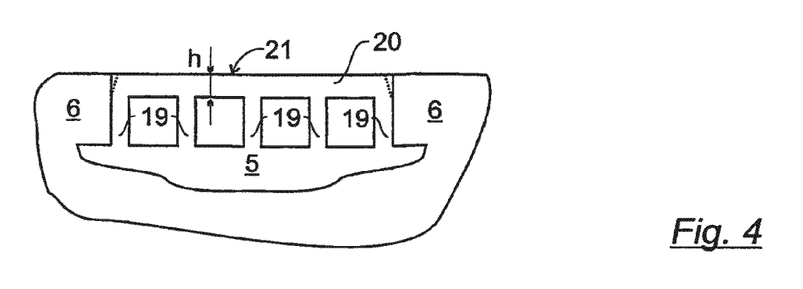
FIG. 4 shows a schematic lateral sectional view of a first laser-sintered or laser-melted layer of the product to be produced, which is connected by means of several supports to a substrate plate situated below.
Figure 5:
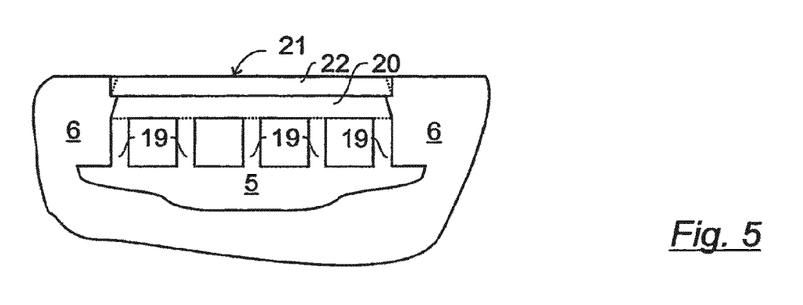
FIG. 5 shows the product of FIG. 4 with a further layer applied.
Figure 6:
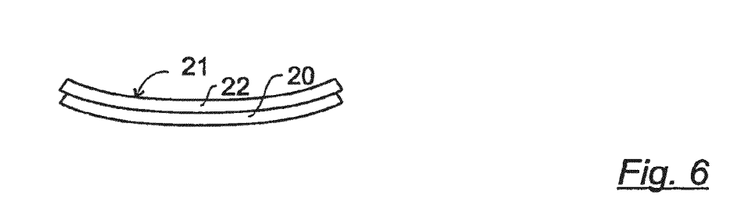
FIG. 6 shows the product of FIG. 5, in a state detached from the supports.

FIGS. 4 to 6 illustrate a further manufacturing-related influence on the dimensional accuracy of the product to be produced.

FIG. 4 shows several supports 19, which have been sintered onto a substrate plate 5, to form the base for a first layer 20 of a product 21 to be produced. This first layer has a height h. The layer 20 cools after the melting. As a result, the layer 20 will contract due to the cooling in accordance with its thermal expansion coefficient. However, the degree of the resulting shrinking of the layer will be greater in the upper region of the layer 20 than in the lower region of the layer 20, since the lower region of the layer 20 is comparatively rigid and thus much less flexible, due to the supports 19 and thus the connection to the substrate plate 5. Thus the upper side of layer 20 shrinks the most. This is illustrated in FIG. 4 by the dashed lines at the lateral ends of layer 20.

FIG. 5 shows that on top of an already cooled layer 20, a further, second layer 22 has been applied, which at its lateral ends due to the cooling shrinks more in the upper region than in the lower region.

A product is composed of a multitude of such layers 20, 22, each of which shrinks due to the cooling and the thermal expansion coefficient and thus generates stresses within the product 21 to be produced.

But it should be noted that the changes in width of the layers due to cooling in FIGS. 4, 5, and 6 are not shown to scale and are greatly exaggerated. This is done to illustrate this manufacturing-related effect.

FIG. 6 shows the product 21 of FIG. 5 after the bottom layer has been detached from the supports 19, for example along the dotted line shown in FIG. 5. As soon as the product 21 is detached from the supports 19, it will deform due to the above-explained stresses within the layers 20, 22. The lateral ends of the product 21 will bend upward after detachment from the supports 19.

This curvature corresponds approximately to a curve described by a $2^{nd}$ degree polynomial.

This effect also can be corrected by means of the compensation data set or the compensation function.

A number of parameters have influence on the deviation of an actual produced product relative to its theoretical planning. The most important parameters are:

Modulus of elasticity, solidus temperature, thermal expansion coefficient, tensile strength, and the elastic yield point of the material, the temperature within the processing chamber during processing, the temperature of the region of the material 6 irradiated by the laser beam, the thickness of layers 12 to 15, 20, 22, the power of laser 7 or the laser beam 8 during the laser sintering or melting, the traverse rate of the laser beam 8, i.e. the speed at which the laser beam is moved along the surface of the material 6, the irradiation strategy, i.e. the manner in which the laser approaches the predetermined points to be irradiated, in some case repeatedly, the geometry, in particular the height of the product 2, 21 to be produced, and the type of a possible secondary treatment of the product after the laser sintering or laser melting.

The listed parameters have different effects on the dimensional accuracy of the product to be produced. For this reason—but also depending on the desired exactness of the product to be produced—it is not necessary to exactly determine all parameters for every case. Even though the achieved results are optimal when all parameters are taken into account, consideration of all parameters increases efforts and costs, which in the final analysis will manifest itself in significantly higher product costs. For this reason, in a particularly preferred embodiment example, only a selection of parameters, i.e. the most influential parameters, are taken into consideration.

Figure 7:
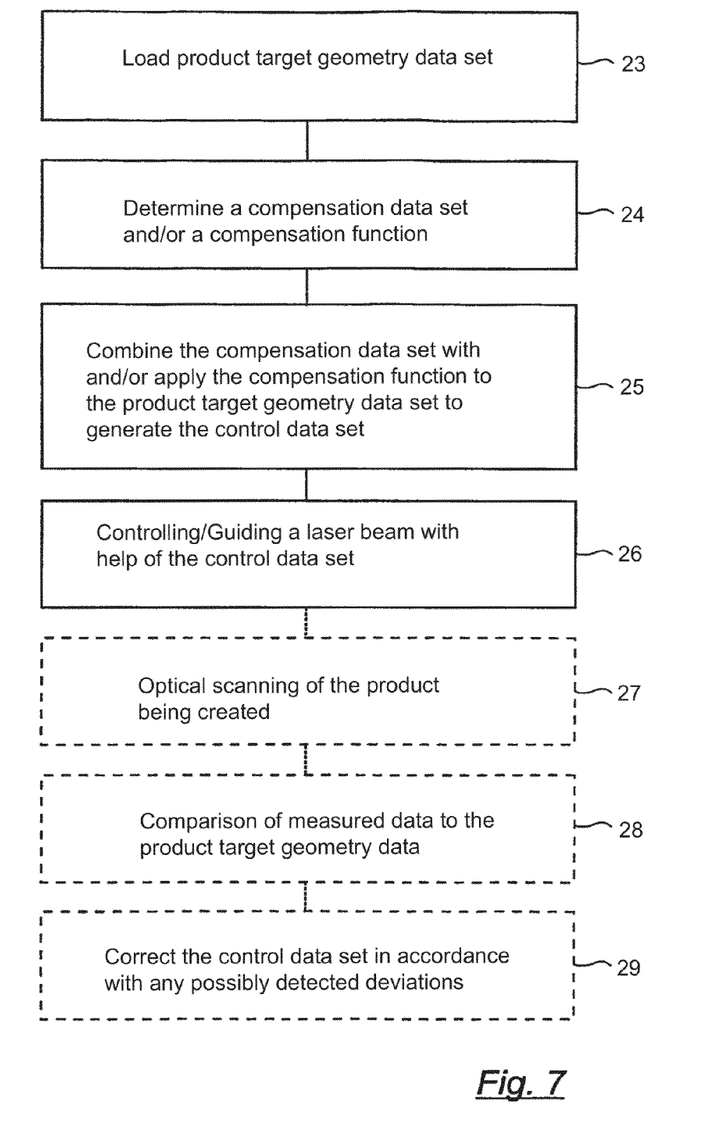
FIG. 7 shows a flow chart as illustration of the processing steps of a method to generate control data sets for the laser beam in accordance with an embodiment example of the invention.

FIG. 7 shows a flow chart as illustration of a method according to an embodiment example of the invention. In a first step 23, the control system loads the target geometry data of a product to be produced. In a further step 24, the control system 11 determines a compensation data set and/or a compensation function. A further step 25 contains the combining of the compensation data set with and/or the applying of the compensation function to the target geometry data of the product to generate a data set to control the laser beam 8. In a further step 26, the laser beam 8 is controlled and guided with the help of this control data set.

In a special embodiment example, the product being created is optically scanned in a further step 27 during the laser sintering or laser melting. In a following step 28, the measurement data obtained in this manner is compared to the target geometry data of the product. In a subsequent step 29, the control data are corrected in accordance with any deviation detected, so that the laser beam will subsequently be controlled and guided with the help of a corrected control data set.

On the whole, the invention has realized that manufacturing-related effects of the laser sintering or laser melting on the products to be produced can be compensated for by manipulating the control data of the laser beam and that in this manner the dimensional accuracy of the products to be produced can be substantially improved.

In the preceding, the invention was explained in connection with laser sintering or laser melting. But the invention is not limited to the use of a laser beam for sintering or melting. An electron beam, for example, can be used instead of a laser beam. Thus, the above-described laser can easily be replaced by an electron beam source. Thus, the invention generally relates to any type of sintering or melting process that is generated by a high-energy beam from a source appropriate for such a high-energy beam.

The invention claimed is:

1. A method for controlling a freeform layer-by-layer production apparatus, whereby a product is built up on a carrier layer by layer, out of a material to be added layer by layer, by means of a high energy beam guided with the help of a control data set, said control data set defining the geometry of the product as it is built up on the carrier only, the method comprising:
loading a product target geometry data set, which represents the target geometry of the product to be produced;
determining, before any freeform sintering and/or freeform melting begins in connection with the product to be produced, a compensation data set and/or a compensation function to compensate for manufacturing-related effects caused by the sintering and/or melting, wherein deformations expected to occur after the product is released from the carrier resulting from stresses within the layers due to different thermal expansion of the layers are calculated and the compensation data set and/or compensation function is determined based on such calculated deformations;
generating the control data set by combining the compensation data set with and/or applying the compensation function to the product target geometry data set to generate the control data set; and
freeform sintering and/or freeform melting by means of the high energy beam in accordance with the control data set;
wherein the compensation function comprises a polynomial of $2^{nd}$, $3^{rd}$, $4^{th}$ and/or higher degree and a plurality of compensation functions when a single product is produced, wherein the plurality of compensation functions at least partially differ with respect to their degree.

2. The method of claim 1, wherein the compensation data set and/or the compensation function is determined in dependence on a size and a shape of the product to be produced.

3. The method of claim 1, characterized in that the compensation function is continuous and differentiable.

4. The method of claim 1, wherein using a plurality of compensation functions includes using a polynomial of lower degree for simple-geometry regions of a product to be manufactured and using a higher degree polynomial for complex geometric regions of a product to be produced.

5. The method of claim 1, wherein applying the compensation function to the product geometry data set includes applying the compensation function to the product geometry data set for only certain regions of the product to be produced.

6. The method of claim 5, wherein the compensation function is applied to the product geometry data set only for the connecting regions of a bridge to be produced as a dental prosthesis.

7. The method of claim 1, wherein the compensation data set and/or the compensation function are determined with the help of at least one parameter selected from a group of parameters consisting of:
a modulus of elasticity of the material;
a solidus temperature of the material;
a thermal expansion coefficient of the material;
a tensile strength of the material;
an elastic yield point of the material;
a processing chamber temperature that represents a temperature in a processing chamber surrounding the material to be processed;
a processing temperature that represents a temperature of a region of the material irradiated by the beam;
a layer thickness that represents a thickness of a material layer that has been or is to be applied;
a power of the beam during sintering or melting;
a traverse rate of the beam;
an irradiation strategy;
a geometry of the product to be produced;
a height of the product to be produced; and
a type of possible secondary treatment of the product after sintering or melting.

8. The method of claim 1, further comprising:
optically scanning, during or after irradiation of a material layer, a contour already created or being created of the product, wherein the optical scanning generates an optical scanning data set;
comparing the optical scanning data set to the product target geometry data set to detect a deviation; and
if a deviation is detected, correcting the control data set in accordance with the detected deviation.

9. Apparatus for the production of metallic and/or non-metallic products by freeform sintering and/or freeform melting by means of a high-energy beam, the apparatus comprising:
a high energy beam source for generating said beam;
a platform to hold a carrier and a material to be deposited in layers onto the carrier;
a control system for controlling the beam according to a control data set to guide the beam to build up a single product from a material layer by layer, the control data set having been generated by calculating deformations that would result from stresses within the layers due to different thermal expansion of the layers expected to occur after the product is released from the carrier, determining the compensation data set and/or compensation function based on such calculated deformations, and combining the compensation data set with and/or applying the compensation function to a product target geometry data set, wherein the compensation data set and/or the compensation function having been determined before any controlling of the beam in connection with the product to be built up;

wherein the compensation function comprises a polynomial of $2^{nd}$, $3^{rd}$, $4^{th}$ and/or higher degree and a plurality of compensation functions when a single product is produced, wherein the plurality of compensation functions at least partially differ with respect to their degree.

10. The apparatus of claim 9, wherein the control data set has been generated so as to guide the beam to produce a dental product.

11. The apparatus of claim 9, wherein the high energy beam source generates a laser beam.

12. The apparatus of claim 9, wherein the high energy beam source generates an electron beam.

13. A method for controlling a freeform layer-by-layer production apparatus whereby a product is built up layer by layer, out of a material to be added layer by layer, by means of a high energy beam guided with the help of a control data set, said control data set defining the geometry of the product as it is built up on the carrier only, the method comprising:

loading a product target geometry data set, which represents the target geometry of the product to be produced;

determining, before any freeform sintering and/or freeform melting begins in connection with the product to be produced, a compensation data set and/or a compensation function to compensate for manufacturing-related melting into a region of a below layer when the layer being produced overhangs the below layer forming an angle of inclination of a plane placed tangentially to an exterior surface of the product relative to a horizontal plane, the compensation data set and/or the compensation function being determined in dependence on the angle of inclination; and generating the control data set by combining the compensation data set with and/or applying the compensation function to the product target geometry data set to generate the control data set; and freeform sintering and/or freeform melting by means of the high energy beam in accordance with the control data set;

wherein the compensation function comprises a polynomial of $2^{nd}$, $3^{rd}$, $4^{th}$ and/or higher degree and a plurality of compensation functions when a single product is produced, wherein the plurality of compensation functions at least partially differ with respect to their degree.

14. The method of claim 13, further comprising using the compensation data set or the compensation function in dependence on the angle of inclination to reduce a thickness of the product to be produced, wherein the thickness is measured perpendicular to said tangential plane.

* * * * *